(12) United States Patent
Compton et al.

(10) Patent No.: US 7,163,673 B2
(45) Date of Patent: Jan. 16, 2007

(54) SUNSCREEN REAGENTS FROM HYDROXY-SUBSTITUTED ACYLGLYCERIDES

(75) Inventors: David L. Compton, Peoria, IL (US); Terry A. Isbell, Elmwood, IL (US); Rogers E. Harry-O'kuru, Peoria, IL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 420 days.

(21) Appl. No.: 10/462,882

(22) Filed: Jun. 17, 2003

(65) Prior Publication Data

US 2004/0258743 A1    Dec. 23, 2004

(51) Int. Cl.
*A61K 7/42* (2006.01)
(52) U.S. Cl. .................... 424/59; 560/105; 560/75; 424/60; 424/450; 424/400; 424/401
(58) Field of Classification Search ............. 424/450, 424/59, 60, 400, 401; 560/105, 75
See application file for complete search history.

(56) References Cited

U.S. PATENT DOCUMENTS 3,052,636 A * 9/1962 Strobel et al. ............. 252/589
3,153,659 A * 10/1964 King ........................ 554/228
4,178,303 A * 12/1979 Lorenz et al. ............. 558/402
5,427,704 A    6/1995 Lawate
5,676,994 A   10/1997 Eskins et al.
5,849,272 A * 12/1998 Baba et al. .................... 424/59
5,882,713 A    3/1999 Eskins et al.
5,979,528 A   11/1999 Tanner et al.
6,017,556 A *  1/2000 Luther et al. .............. 424/450
6,346,236 B1 * 2/2002 Compton et al. ............. 424/60

FOREIGN PATENT DOCUMENTS

WO    WO 02/079121    10/2002

OTHER PUBLICATIONS

Freitas et al., Glyceridic Esters of p-Methyoxycinnamic Acid. A New Sunscreen of the Cinnamate Class, International Journal of Cosmetic Science, 2001, 23, 147-142.*
Compton et al., Lipase-catalyzed synthesis of Ferulate Esters, JAOCA, 2000, 77, 5, 513-519.*
Terry A. Isbell et al., Synthesis of Triglyceride Estolides from Lesquerella and Castor Oils, JAOCS, vol. 79, No. 12 (2002).

* cited by examiner

*Primary Examiner*—Thurman K. Page
*Assistant Examiner*—Chukwuma Nwaonicha
(74) *Attorney, Agent, or Firm*—John D. Fado; Randall E. Deck; Lesley Shaw

(57) ABSTRACT

A class of UVA- and UVB-absorbing esters has been derived by modifying hydroxy triglycerides and other acyltriglycerides with any of a variety of cinnamic acids. The esterification reactions are preferably conducted at elevated temperatures without a catalyst. The resultant agents have the advantage of being synthesized from natural materials, while providing a value-added use for the oil. They are readily formulated into standard UV-absorbing daily-wear cosmetic, hair and skin care, and sunscreen formulations.

24 Claims, No Drawings

SUNSCREEN REAGENTS FROM HYDROXY-SUBSTITUTED ACYLGLYCERIDES

CROSS REFERENCE TO RELATED APPLICATION

This application is related to commonly assigned application Ser. No. 10/463,491, filed concurrently herewith, by Rogers E. Harry-O'kuru entitled "Novel Sunscreen Reagents from Unsaturated Waxes and Triglycerides", herein incorporated by reference in its entirety.

BACKGROUND OF THE INVENTION

1. Field of the Invention

This invention relates to modification of hydroxy acylglycerides with cinnamic acids to form ultraviolet (UV)-A and (UV)-B absorbing esters. In an exemplary embodiment, naturally-occurring hydroxy triglycerides, such as lesquerella and castor oils, are converted to cinnamic-triglyceride esters at high temperatures (200° C.) without a catalyst.

2. Description of the Prior Art

Health hazards associated with exposure to the sun are well established. The short term effect of excessive exposure to sunlight is erythema, commonly referred to as sunburn. Sunburn is primarily the result of UVB radiation having a wavelength of from about 290 nm to about 320 nm. Long term effects of exposure to sunlight include skin cancer (melanoma) and premature aging of the skin (including wrinkling, loss of elasticity, and pigment changes). These effects are predominantly caused by UVA radiation having a wavelength of from about 320 nm to about 400 nm. Public awareness of the dangers of sun exposure has stimulated the market for personal care products containing sunscreens.

Sunscreens function either as ultraviolet (UV) filters or UV blocks. UV blocks, such as $TiO_2$ and ZnO, as well as derivatives of other metal-oxides, form a physical barrier that scatters UV light (Fairhurst et al., "Particulate Sun Blocks: General Principles", Sunscreens: Development, Evaluation, and Regulatory Aspects 2nd Edn, pp. 313–352, 1997). These UV blocks offer the most comprehensive sunscreen protection, blocking the full spectrum of UVA (400–320 nm) and UVB (320–290 nm) light. As a result of the particulate nature of these formulations, they often leave a noticeable residue when applied to the skin, which is cosmetically unacceptable to the consumer. The most commonly used sunscreens are UV filters, which are typically organic compounds incorporated at levels of about 2–15% into topical formulations (N. A. Shaath, "Evolution of Modern Sunscreen Chemicals", Ibid, pp. 3–33, 1997), (N. A. Shaath, "Quality Control of Sunscreens", Ibid, pp. 657–676, 1997). A disadvantage of UV filters is that each organic compound has a limited range of maximum UV absorptivity, rendering each reagent better suited for either UVA protection or UVB protection but not both. The advantage of the UV filtering molecules, however, is that they can be engineered to provide sunscreens with desirable physical appearance, solubility, and water resistant properties (N. A. Shaath, "Quality Control of Sunscreens", Ibid, pp. 657–676, 1997).

Although no longer used today, benzyl cinnamate formulated as an emulsion with benzyl salicylate, was used as a sunscreen as early as 1928 (N. A. Shaath, "Evolution of Modern Sunscreen Chemicals", Ibid, pp. 3–33, 1997). Today, cinnamic acid derivatives are the most widely used UVB absorbing chemicals in sunscreen formulations, with four derivatives approved for use in the United States and 17 approved for use in Europe (N. A. Shaath, "Evolution of Modern Sunscreen Chemicals", Ibid, pp. 3–33, 1997). The unsaturated C=C bond adjacent to the aromatic ring in cinnamates allows for a continuous, conjugated p-system throughout the molecule. An electron can be delocalized throughout the p-system by photo-excitation with energy corresponding to about 305 nm. Most common cinnamic acids and short chain esters are water soluble, limiting their usefulness as waterproof sunscreens. Cinnamic acid derivatives, therefore, have been designed with long chain hydrocarbons (i.e. octyl-p-methoxy cinnamate), which renders them water-insoluble and suitable for waterproof sunscreens. The $—OCH_3$ group of octyl-p-methoxy cinnamate acts as an electron-releasing group to improve the electron excitation process (N. A. Shaath, "Evolution of Modern Sunscreen Chemicals", Ibid, pp. 3–33, 1997).

There is currently a growing interest in modifying fats and oils to form structured lipids with specific properties for nutritional and pharmaceutical applications. Recent reviews have outlined the strategies for synthesizing tailor-made fats and oils and their desired properties (Willis et al., "Lipid Modification Strategies in the Production of Nutritionally Functional Fats and Oils", Crit. Rev. Food Sci. Nutr. 38:639–674, 1998), (F. D. Gunstone, "Movements Towards Tailor-Made Fats", Prog. Lipid. Res. 37:277–305, 1998). These strategies have included blending, distillation, fractionation, hydrogenation, interesterification with chemical catalysts, and more recently interesterification with biocatalysts. Chemical interesterifications of triacylglycerols for industrial applications are typically performed using inorganic catalysts at elevated temperatures (200–250° C.) (N. N. Gandhi, "Applications of Lipase", J. Am. Oil Chem. Soc. 74:621–633, 1997). Enzymatic interesterifications, however, offer the advantages of milder reaction conditions, a wider variety of synthetic substrates, and regioselective specificity towards the acyl groups of the triglycerols (Schmid et al., "Lipases: Interfacial Enzymes with Attractive Applications", Angew. Chem. Int. Ed. 37:1608–1633, 1998).

Compton et al. (U.S. Pat. No. 6,346,236 hereby incorporated by reference) teaches the formation of sunscreens from vegetable oil and plant phenols by use of a lipase catalyzed transesterification reaction to yield novel ferulyl-substituted or coumaryl-substituted acylglycerols.

SUMMARY OF THE INVENTION

We have now invented a novel class of UVA- and UVB-absorbing compounds derived from hydroxy triglycerides and other hydroxy-substituted acylglycerols that are reacted with a variety of cinnamic acids. These agents have the advantage of being synthesized from natural materials, while providing a value-added use for vegetable oils. Moreover, they can be produced at elevated temperatures (~200° C.) without a catalyst, thereby avoiding any concern about undesirable residues in the final product. These agents are readily formulated into standard UV-absorbing daily-wear cosmetic, hair and skin care, and sunscreen formulations.

The starting materials utilized in creating the compounds of this invention are generally characterized as being any hydroxy-substituted triglyceride oil. Of particular interest, without limitation thereto, are naturally-occurring hydroxy triglycerides, such as lesquerella and castor oils.

In accordance with this discovery, it is an object of this invention to provide feruloyl-, coumaroyl-, sinapoyl-, or o-methylsinapoyl-substituted acylglycerols, having utility as sunscreen and antioxidants agents.

It is a further object of this invention to provide a facile and efficacious method of producing the subject sunscreen and antioxidant agents by means of a simple reactive process in the absence of a chemical catalyst.

It is also an object of the invention to produce a sunscreen agent that provides broad spectrum UV (both UVA and UVB) protection.

Another object of the invention is to incorporate the feruloyl, coumaroyl, sinapoyl- or o-methylsinapoyl-substituted acylglycerols of the invention into daily-wear cosmetic, hair and skin care, and sunscreen formulations.

A further object of the invention is to produce sunscreen agents that have the advantage of being synthesized from natural materials, while providing value-added use for vegetable oils.

Other objects and advantages of this invention will become readily apparent from the ensuing description.

DETAILED DESCRIPTION

The substituted acylglycerols of the invention consist of acylglycerols in which one or more of the acyl substituents are substituted with one or more cinnamic acid moieties, selected from the group of feruloyl, coumaroyl, sinapoyl, and o-methylsinapoyl moieties. Sunscreen agents of the invention are illustrated by Formula I, and include mono-, di-, and tri-acylglycerols wherein at least one of $R_1$, $R_2$, or $R_3$ is an acyl moiety substituted with one or more feruloyl, coumaroyl, sinapoyl, and o-methylsinapoyl moieties at various locations on each chain. The remaining positions ($R_1$, $R_2$, or $R_3$) can be any combination of acyl moieties, aliphatic moieties, and hydrogen.

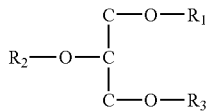

Formula I

Preferably the acylglycerol is a triglyceride, particularly a natural vegetable oil. These oils may have fatty acid moieties ranging in length from C2–C26, preferably C12–C26 and most preferably, C16–C22. The fatty acid moieties (residues) on a given acylglyceride molecule may have varying degrees of saturation, from completely saturated (defined herein for purposes of this application to include hydroxy substituted) to tri-unsaturated, with the proviso that at least some of the fatty acid moieties in a given oil sample are hydroxy-substituted. Exemplary natural oils that are naturally hydroxylated and are useful as starting materials for this invention include lesquerella oil (high in lesquerolic acid) and castor oil (high in ricinoleic acid) wherein the hydroxy moiety occurs on C14 or C12, respectively.

The sunscreen compounds of the invention are produced in a reaction between hydroxy-containing acylglycerides and ferulic, coumaric, sinapic, and o-methylsinapic acid, the structures of which are shown, below. The natural isomers of plant phenols are trans at the olefinic group; however, it is envisioned that the feruloyl, coumaroyl, sinapoyl, and o-methylsinapoyl moieties used herein could also be cis.

Strutures of Various Cinnamic Acids

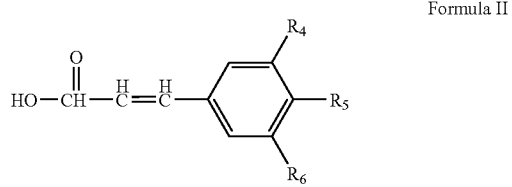

Formula II $R_4, R_5, R_6 = H$     cinnamic acid
$R_4 = H; R_5 = OH; R_6 = OCH_3$     ferulic acid
$R_4, R_6 = OCH_3; R_5 = OH$     sinapic acid
$R_4, R_6 = H; R_5 = OH$     coumaric acid
$R_4, R_5, R_6 = OCH_3$     o-methylsinapic acid Esterification of acid moieties with the hydroxy-substituted fatty acid moiety is optimally conducted in the absence of oxygen, such as in vacuo or under nitrogen, and without the use of a catalyst or a solvent. The fatty acid or acylglyceride is reacted with ferulic, coumaric, sinapic or o-methylsinapic acid at a temperature ranging from about 150° C. to about 250° C. for a period of time ranging from about 12 to 72 hours.

Scheme 1, below, illustrates the esterification process contemplated by the invention by showing the single step involved in the esterification of the main triglyceride component of lesquerella oil with ferulic acid to produce the ferulyl-lesquerella ester.

Scheme 1

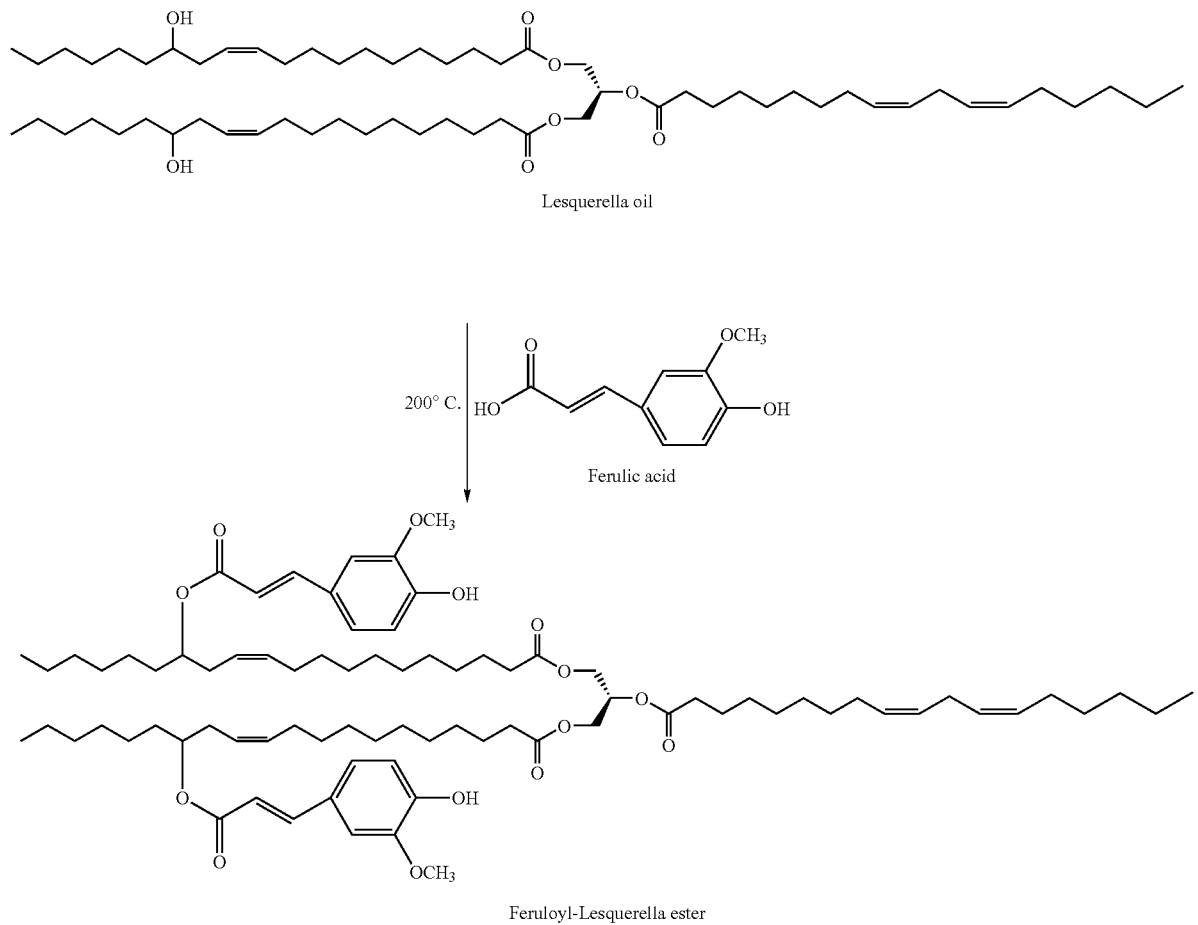

The cinnamoyl-substituted acylglycerols of this invention are characterized by the properties of having the UV absorptivity of a cinnamate ester and the water-insoluble properties of a lipid, thereby rendering them useful as sunscreen agents for the skin that do not readily wash off with water. The UV absorbance of these products extends from about 280 nm to about 350 nm, and they are particularly effective in absorbing UV in the range of about 310 nm to about 350 nm. This is predominantly in the UVA range, but also covers part of the UVB range. For additional UVB protection, the subject compounds may be formulated with other sunscreen agents as discussed, below.

The sunscreen agents of the invention as defined by the general Formula I, as shown above, may be formulated into any cosmetic preparations that are especially designed to be water-resistant. The total level of sunscreen agent in these preparations will typically be on the order of about 0.1 to 20%, by weight, and preferably within the range of about 1 to about 15%, by weight. The amount of sunscreen agent currently approved in the United States for inclusion in a topical skin treatment formulation is 15% by weight. It is contemplated that the agents of this invention will be incorporated into formulations that are both effective and safe. An effective amount (or photoprotective amount) is that amount which is sufficient to significantly induce a positive effect of protection against UV sunlight as compared to a control. One measure of the effectiveness of the sunscreen agent is the Sun Protection Factor (SPF) of the composition. SPF is a commonly used measure of photoprotection of a sunscreen against sunburn. The SPF is defined as the ratio of the UV energy required to produce minimal erythema on protected skin to that required to produce the same minimal erythema on unprotected skin in the same individual. See Federal Register, 43, no. 166, pp. 38206–38269, Aug. 25, 1978). A safe amount is that which does not produce serious side effects.

The cosmetic preparations according to the invention can be formulated as a lotion, cream, gel, stick or aerosol. The base of the formulation may be a water-in-oil emulsion, an oil-in-water emulsion, an oil-in-oil alcohol lotion, a vesicular dispersion, or as an emulsifier-free starch/lipid dispersions as described in U.S. Pat. Nos. 5,676,994 and 5,882,713, both herein incorporated by reference. The term "oil" is used herein to be inclusive of all lipids. The term "lipid" (or fat) is a comprehensive term referring to substances which are found in living cells and which are comprised of only a non polar hydrocarbon moiety or a hydrocarbon moiety with polar functional groups (see the Encyclopedia of Chemistry, 3rd Edition, C. A. Hampel and G. G. Hawley, eds., 1973, p. 632, herein incorporated by reference). Most lipids are insoluble in water and are soluble in fat solvents such as ether and chloroform. Commonly used oils for cosmetic formulations include coconut oil, silicone oil and jojoba oil.

Other components that may be included in the sunscreen formulations of the invention include: other UVA and UVB sunscreen agents, such as 2-phenyl-benzimidazole-5-sulfonic acid, TEA salicylate, octyl dimethyl PABA, padimate-O (2-ethylhexyl 4-(dimethylamino) benzoate) and octyl methyl cinnamate; inorganic physical sunblocks, such as zinc oxide and $TiO_2$; artificial tanning agents; abrasives; absorbents; fragrances; pigments; colorings/colorants; essential oils; skin sensates; astringents carriers and vehicles; thickening/structuring agents; emollients; emulsion stabilizers; excipients and auxiliaries commonly incorporated into cosmetic formulations; humectants; moisturizers; skin conditioners; anti-caking agents; antifoaming agents; antimicrobial agents; antioxidants; binders; buffering agents; bulking agents; chelating agents; chemical additives; film formers; humectants; opacifying agents; skin-conditioning agents; vitamins; and the like. Suitable emulsifiers include any of those conventionally used for cosmetic formulations, including for example, ethoxylated esters of natural derivatives, such as polyethoxylated esters of hydrogenated castor oil, a silicone oil emulsifier such as silicone polyol, free or ethoxylated fatty acid soap, an ethoxylated fatty alcohol, a free or ethoxylated sorbitan ester, an ethoxylated fatty acid or an ethoxylated glyceride. Exemplary agents and additives that could be included in formulations comprising the sunscreen agents of the invention, as well as suggested levels of addition, are given in U.S. Pat. No. 5,989,528 (Tanner et al.), which is herein incorporated by reference.

As previously indicated, the compositions of the invention are useful as sunscreen agents to provide protection from adverse effects of UV radiation. The principal application is as a topical sunburn protectant for human skin. However, it is envisioned that the compositions and formulations of the invention would also have veterinary applications as a skin protectant. The sunscreen formulations contemplated herein may be applied to the skin by spreading or spraying a thin layer thereof over the skin surface intended to be protected.

It is envisioned that the compounds of this invention may also have certain industrial applications, such as a UV protectant for epoxies, paints, and other consumer products. For these applications, the compounds could either be formulated into the material to be protected, such as by blending into a paint, or they could be applied as a separate coating.

The following example is intended to further illustrate the invention, without any intent for the invention to be limited to the specific embodiments described therein.

EXAMPLE 1

Synthesis of Cinnamoyl-Lesquerella Esters

Pressed, refined, and degassed lesquerella oil (1.0 mL, 1.0 mM), cinnamic acid (288 mg, 2 mM), and activated 3 Å molecular sieves (220.0 mg) were placed in a 5 mL glass ampule (Kimble Glass, Inc., Vineland, N.J.) under a nitrogen atmosphere. The ampule was sealed under a stream of nitrogen using a two-gas micro-torch (5000° F., Microflame Inc., Minnetonka, Minn.). The ampule was buried in a sand bath that was heated via a heating mantel and temperature controlled using a Variac controller. The ampule was removed and the contents periodically agitated to ensure a homogeneous reaction mixture. After 24 hours the ampule was allowed to cool to ambient temperature, the seal broken, and the contents extracted with three 1 mL portions of hexane. The combined extracts were filtered though a bed of Celite, the bed was then rinsed with three portions of 1 mL of hexane, and the washings combined with the filtrate. The solvent was removed from the filtrate under vacuum, and the final residue was dried in vacuo at 75° C. for 18 hours. Unreacted cinnamic acid sublimed from the final residue. The cinnamoyl-lesquerella ester yield, determined by $^1$H NMR data (see Isbell, T. A. and Cermak, S. C. "Synthesis of Triglyceride Estolides from Lesquerella and Castor Oils" J. Am. Oil Chem. Soc. 2002, 79, 1227–1233) was 87%. Table 1 reports the yields of similar reactions, varying the type of oil and the molar ratio of the cinnamic acid.

All references disclosed herein or relied upon in whole or in part in the description of the invention are incorporated by reference.

TABLE 1

Yields of Lesquerella- and Castor-Cinnamate Ester Reactions performed at 200° C. for 24 hours

| Oil | Molar Equiv. of Cinnamic acid | Molecular Seives (mg) | Yield (%) |
| --- | --- | --- | --- |
| Lesquerella | 2 | 320 | 87 |
| Lesquerella | 3 | 320 | 97 |
| Castor | 3 | 500 | 86 |
| Castor | 4 | 500 | 92 |

The invention claimed is:

1. A compound having the structural formula:

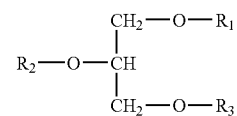

wherein $R_1$, $R_2$ and $R_3$ are independently selected from the group consisting of (1) a C2–C26 aliphatic residue; (2) a C2–C26 acyl residue; (3) a C2–C26 aliphatic residue substituted with one or more cinnamate moieties selected from the group consisting of cinnamoyl, feruloyl, coumoroyl, sinapoyl, and o-methylsinapoyl; (4) a C2–C26 acyl residue substituted with one or more cinnamate moieties selected from the group consisting of cinnamoyl, feruloyl, coumoroyl, sinapoyl, and o-methylsinapoyl, and (5) hydrogen, with the proviso that at least one of said $R_1$, $R_2$ and $R_3$ is one of the C2–C26 acyl or C2–C26 aliphatic residues substituted with one or more cinnamate moieties.

2. The compound of claim 1, wherein at least one of said cinnamate moieties is cinnamoyl.

3. The compound of claim 1, wherein at least one of said cinnamate moieties is feruloyl.

4. The compound of claim 1 wherein at least one of said cinnamate moieties is o-methylsinapoyl.

5. The compound of claim 1, wherein at least one of said $R_1$, $R_2$ or $R_3$ aliphatic or acyl residues is C12–C22.

6. The compound of claim 5, wherein at least one of said $R_1$, $R_2$ or $R_3$ is a ricinoleic acid residue.

7. The compound of claim 5, wherein at least one of said $R_1$, $R_2$ or $R_3$ is a lesquerolic acid residue.

8. The compound of claim 5, wherein at least one of said at least one of said $R_1$, $R_2$ or $R_3$ is an aliphatic moiety.

9. The compound of claim 5 wherein at least one of said $R_1$, $R_2$ or $R_3$ is hydrogen.

10. The compound of claim 5, wherein at least two of said $R_1$, $R_2$ or $R_3$ are hydrogen.

11. A sunscreen formulation comprising:
a sunscreen agent having the structure:

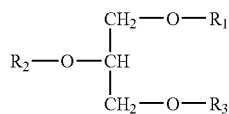

wherein $R_1$, $R_2$ and $R_3$ are independently selected from the group consisting of (1) a C2–C26 aliphatic residue; (2) a C2–C26 acyl residue; (3) a C2–C26 aliphatic residue substituted with one or more cinnamate moieties selected from the group consisting of cinnamoyl, feruloyl, coumoroyl, sinapoyl, and o-methylsinapoyl; (4) a C2–C26 acyl residue substituted with one or more cinnamate moieties selected from the group consisting of cinnamoyl, feruloyl, coumoroyl, sinapoyl, and o-methylsinapoyl, and (5) hydrogen, with the proviso that at least one of said $R_1$, $R_2$ and $R_3$ is one of the C2–C26 acyl or C2–C26 aliphatic residues substituted with one or more cinnamate moieties; and a carrier for the sunscreen agent, wherein said agent is present in said formulation in a photoprotective amount.

12. The formulation of claim 11, wherein at least one of said cinnamate moieties is cinnamoyl.

13. The formulation of claim 11, wherein at least one of said cinnamate moieties is feruloyl.

14. The formulation of claim 11, wherein at least one of said cinnamate moieties is o-methylsinapoyl.

15. The formulation of claim 11, wherein at least one of said $R_1$, $R_2$ or $R_3$ aliphatic or acyl residue is C12–C22.

16. The formulation of claim 11, wherein at least one of said $R_1$, $R_2$ or $R_3$ is a ricinoleic acid residue.

17. The formulation of claim 11, wherein at least one of said $R_1$, $R_2$ or $R_3$ is a lesquerolic acid residue.

18. The formulation of claim 11, wherein at least one of said $R_1$, $R_2$ and $R_3$ is an aliphatic moiety.

19. The formulation of claim 11, wherein at least one of said $R_1$, $R_2$ and $R_3$ is hydrogen.

20. The formulation of claim 11 wherein at least two of said $R_1$, $R_2$, and $R_3$ are hydrogen.

21. The formulation of claim 11, wherein said agent is present in an amount of at least 0.1% by weight.

22. The formulation of claim 11, wherein said agent is present in an amount of 0.1% to 20% by weight.

23. A method of making a compound having the structural formula:

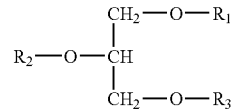

wherein $R_1$, $R_2$ and $R_3$ are independently selected from the group consisting of (1) a C2–C26 aliphatic residue; (2) a C2–C26 acyl residue; (3) a C2–C26 aliphatic residue substituted with one or more cinnamate moieties selected from the group consisting of cinnamoyl, feruloyl, coumoroyl, sinapoyl, and o-methylsinapoyl; (4) a C2–C26 acyl residue substituted with one or more cinnamate moieties selected from the group consisting of cinnamoyl, feruloyl, coumoroyl, sinapoyl, and o-methylsinapoyl, and (5) hydrogen, with the proviso that at least one of said $R_1$, $R_2$ and $R_3$ is one of the C2–C26 acyl or C2–C26 aliphatic residues substituted with one or more cinnamate moieties;

comprising the steps:
a) heating a mixture of a naturally-occurring, hydroxy-containing acylglyceride in the presence of an acid selected from the group consisting of cinnamic acid, ferulic acid, coumaric acid, sinapic acid, and o-methylsinapic acid at an elevated temperature to produce said compound; and
b) recovering said compound from said heated mixture.

24. The method of claim 23, wherein said heating is carried out in the absence of oxygen, in vacuo, or under nitrogen.

* * * * *